United States Patent [19]

Kamarei et al.

[11] Patent Number: 4,879,312

[45] Date of Patent: Nov. 7, 1989

[54] METHOD FOR ENHANCING OR PROVOKING ANGIOGENESIS USING ANGIOGENICALLY ACTIVE OMEGA-3 POLYUNSATURATED FATTY ACIDS

[75] Inventors: Ahmad R. Kamarei, Lexington; Michael Klibaner, Brookline; Denise Peton, Boston, all of Mass.

[73] Assignee: Angio Medical Corporation, New York, N.Y.

[21] Appl. No.: 164,789

[22] Filed: Mar. 7, 1988

[51] Int. Cl.$^4$ ............................................. A61K 31/20
[52] U.S. Cl. .................................................... 514/560
[58] Field of Search ................................ 514/558, 560

[56] References Cited

U.S. PATENT DOCUMENTS 4,447,418  5/1984  Maddoux ............................ 424/165
4,678,808  7/1987  Ward et al. ......................... 514/822
4,699,788  10/1987  Catsimpoolas et al. ............ 424/104

Primary Examiner—Jerome D. Goldberg
Assistant Examiner—Raymonod J. Henley III
Attorney, Agent, or Firm—Felfe & Lynch

[57] ABSTRACT

The invention teaches the provocation or enhancement of angiogenesis in a subject via the administration of angiogenically active omega-3 polyunsaturated fatty acids. Especially preferred are eicosapentaenoic acid (EPA) and docosahexaenoic acid (DHA).

8 Claims, 8 Drawing Sheets

Fig. 1.

EPA

DHA

CAM ASSAY OF EICOSAPENTAENOIC ACID (EPA)

Fig. 10.

CAM ASSAY OF DOCOSAHEXAENOIC ACID (DHA)

Fig. 11.

METHOD FOR ENHANCING OR PROVOKING ANGIOGENESIS USING ANGIOGENICALLY ACTIVE OMEGA-3 POLYUNSATURATED FATTY ACIDS

FIELD OF THE INVENTION

This invention relates to a method for causing or increasing angiogenesis in a subject in need of angiogenesis or increased angiogenesis via administration of an angiogenically effective amount of a pharmaceutically acceptable omega-3 polyunsaturated fatty acid with angiogenic activity.

BACKGROUND AND PRIOR ART

Interest in angiogenesis is evidenced by the vast amount of literature available on the subject, some of which is over one hundred years old. See, e.g., Virchau, R., Die Krankhaftern Geshwulste, Hirshwald, Berlin (1863); Thierisch, C., Die Hautmit Altas, Leipzig (1865). "Angiogenesis" is defined as the process by which new blood vessels are formed, with accompanying increased blood circulation. Much of the research in this field over the past ten years has concentrated on identifying and purifying naturally occurring substances which cause angiogenesis. Examples of the literature in this area include Weiss, et al., Br. J. Cancer 40: 493-96 (1979); Fencelau, et al., J. Biol. Chem. 256: 9605-9611 (1981); McAslan, et al., Exp. Cell Res. 119: 181-190 (1979), which show that angiogenic factors are present in tissues of pathological origin, such as tumor cells. Kuma,, et al., Lancet 2: 364-367 (1983); and Brown, et al., Lancet 1: 682-685 (1980), show an angiogenesis factor in synovial fluid of arthritis patients, while Hill, et al., Experentia 39: 583-585 (1983) show one in vitreous of arthritic patients. Banda, et al., Proc. Natl. Acad. Sci. 79: 7773-7777 (1982), teach one in wound fluid. Additional teachings in this field include those of D'Amore, et al., Proc. Natl. Acad. Sci. 78: 3068-3072 (1981); Kissun, et al., Br. J. Ophthalmol. 66: 165-159 (1982); DeCarvellho, et al., Angiology 34: 231-243 (1983); Frederick, et al., Science 224: 289-290 (1980); Burgos, Eur. J. Clin. Invest 13: 289-296 (1983); and Catellot, et al., Proc. Natl. Acad. Sci. 79: 5597-5601 (1982), all of which show the existence of angiogenic factors in normal tissues.

Characteristic of all of the angiogenic materials discussed in the above referenced prior art is that they are involved in normal growth and development. In other words, angiogenesis is a necessary process during the growth and development of an individual organism. The prior art angiogenic factors described supra are involved in these normal processes, but are apparently not implicated in enhanced rates of angiogenesis, which is sometimes necessary or desirable.

One of the first endeavors involving investigation of lipid factors provoking enhanced angiogenesis is to be found in Goldsmith, et al., JAMA 252: 2034-2036 (1984). The factor was found in chloroform-methanol fractionates of feline omentum. This research is presented in U.S. Pat. No. 4,699,788, the disclosure of which is incorporated herein. This extract is a lipid extract.

Additional research based upon the teachings of Goldsmith, et al. found that the class of glycolipids known as gangliosides possesses enhanced angiogenic activity. This may be seen in U.S. Pat. No. 4,710,490, the disclosure of which is incorporated by reference herein.

It will be seen that the newest research on angiogenesis points to lipid containing molecules as provoking enhanced angiogenesis. This was new to the art, as the earlier literature all suggested that protein derived material caused angiogenesis. Thus, Kumar, et al., Lancet 2: 364-367 (1983) teach proteins of from 300 to $10^5$ daltons, while Kissun, et al., Br. J. Ophthalmol 66: 165-169 (1982), show protein factors weighing up to 70 kilodaltons. Banda, et al., Proc. Natl. Acad. Sci. 79: 7773-7777 (1982), teach proteins of from 2 to 14 kilodaltons as provoking angiogenesis and Burgos, et al., Eur. J. Clin. Invest 13: 289-296 (1983), show protein complexes of from 100 to 200 kilodaltons. A very recent report, by van Brunt, et al., Biotechnology 6(1): 25-30 (Jan. 1988) describes angiogenesis caused by proteins.

The art, however, contains no mention of omega-3 polyunsaturated fatty acids as angiogenic substances.

Figure 1:
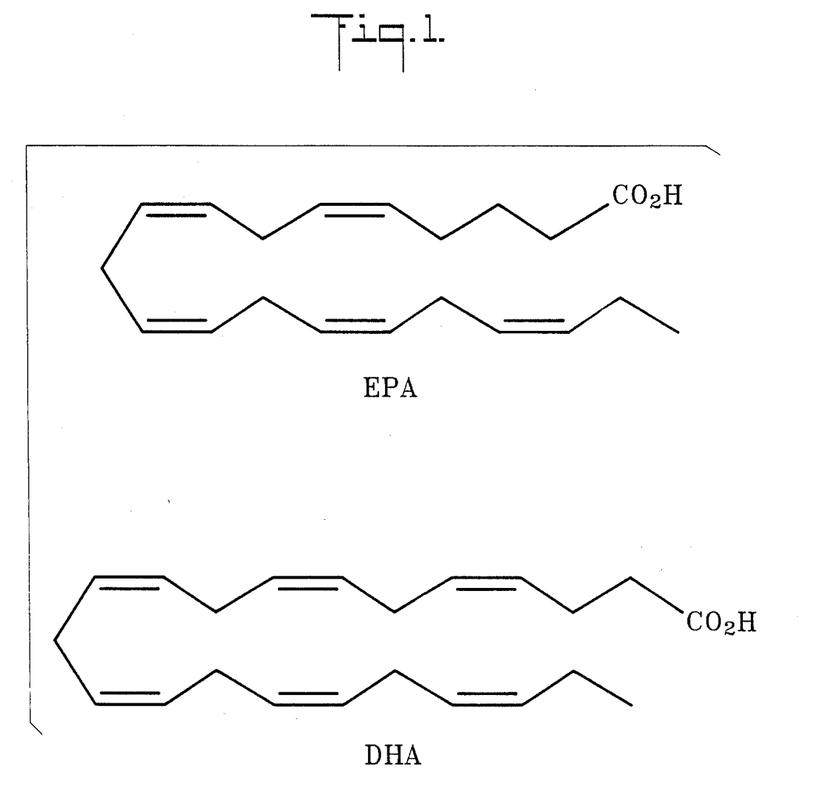
FIG. 1 gives structural formulas for eicosapentaenoic acid and docosahexaenoic acid.

The class of lipid molecules known as "omega 338, "ω-3" or "n-3" polyunsaturated fatty acids ("n-3 PUFAs") have been studied in various contexts. Omega-3 is a shorthand notation that designates the positional arrangement of the double bonds closest to the terminal methyl group (FIG. 1).

The omega-3 family is obtained mainly from dietary seafood or can be derived from linolenic acids which occur in leafy vegetables and unhydrogenated soybean oil. The levels of omega-3 in human tissues are low except for those people consuming large quantities of seafood and in particular the 20:5ω3 (EPA) and 22:6ω3 (DHA). Evidence shows that members of the Greenland Eskimo population, who consume a diet rich in seafood, as compared to their conterparts living in Denmark, have a higher amount of omega-3 present. (Dyerberg, J. 1981, Phil trans. Royal Soc. London B294: 373; Jorgensen K. A. and Dyerberg, J. 1982 Adv. Nutr. Res. 5:57; Lee, 1985 et al, New Eng. J. Med. 312:1217).

Much evidence shows that a diet rich in omega-3 fatty acids has beneficial effects in humans, including a reduction in plasma cholesterol and triglycerides levels, improved fat tolerance, prolonged bleeding time, reduced platelet counts and decreased platelet adhesiveness (Lee et al, supra; Phillpson et al, 1985 New Eng. J. Med. 312: 1210). Of primary interest is the effect of these fatty acids on heart disease. Thus, Kinsella, in Food Technology: 89-97, 146 (February 1986), summarizes the literature on n-3 PUFAs as obtained from fish. This reference explores the various biochemical pathways in which the n-3 PUFAs participate, and suggests some of the reasons why these materials may be involved in alleviating ischemic heart disease. In a similar vein, Saynor, et al., Atheriosclerosis 50: 3-10 (1984) discuss the role of one n-3 PUFA, i.e., eicosapentaenoic acid ("EPA") in reducing triglyceride and very low density lipoprotein (VLDL) serum levels. The paper also shows, however, that bleeding time increased, and the ability of platelets to aggregate decreased when EPA was administered.

Terano, et al, Atheriosclerosis 46: 321-331 (1983) comment on the same effects, but also state that EPA reduces whole blood viscosity.

The patent literature on the n-3 or ω-3 PUFAs is scant. Rubin, U.S. Pat. No. 4,526,902, teaches the treatment of thrombo-embolic conditions using a combination of one of EPA (5, 8, 11, 14, 17-eicosapentaenoic acid), and DHA (22:6 ω-3 docosahexaenoic acid) and a linoleic acid derivative. Of interest in this reference, the content of which is incorporated herein, is the teaching that mixtures of EPA and DHA/linoleic acid derivatives need not be administered as pharmaceuticals, but that they can also be administered in food form, such as cooking oil or margarine. Debat, U.S. Pat. No. 4,186,211, teach that higher alkanols and their esters can be used to treat prostate conditions. No ω-3 PUFAs are taught; rather docosa- and eicosaalkanol derivatives are the active compositions.

It will be seen then, that none of the prior art teaches or suggests that omega-3 polyunsaturated fatty acids may be used to provoke or to enhance angiogenesis.

Hence it is an object of the invention to provide a method for provoking or enhancing angiogenesis in an individual subject by administering to the subject an angiogenically effective amount of an angiogenically active ω-3 polyunsaturated fatty acid. Especially preferred are methods of treatment utilizing eicosapentaenoic acid (EPA), and docosahexaenoic acid (DHA). How the objects of this invention are achieved will be seen via review of the disclosure which now follows.

DETAILED DESCRIPTION OF PREFERRED EMBODIMENTS

The following presents the results of experiments which show that the ω-3 polyunsaturated fatty acids, especially eicosapentaenoic acid (EPA), and docosahexaenoic acid (DHA) cause angiogenesis in subjects to which they are administered in angiogenically effective amounts.

The results were obtained using two, distinct methods: the chicken chorioallantoic membrane assay ("CAM" assay), and the rabbit cornea assay. The CAM assay is described by, e.g., Auerbach, et al., Developmental Biology 41: 391 (1974); as well as in U.S. Pat. Nos. 4,699,788, and 4,710,490 the disclosures of which are incorporated by reference. The rabbit cornea assay is described in Alderman, et al., Biochemistry 24: 7866 (1986).

EXAMPLE 1: CAM Assays

In order to test samples, as well as controls, methyl cellulose pellets were used. These pellets were prepared by first autoclaving a sample of methyl cellulose dry, followed by dissolving (2% w/v) in sterile distilled water. This solution was mixed by overnight stirring.

The methyl cellulose solution was used to prepare both the control pellets used in the CAM assays, as well as the sample pellets.

To prepare sample pellets, methylcellulose solution was poured onto 100 mm. Petri dish covers, and this solution was then allowed to dry. The dried methyl cellulose formed a thin layer which was cut into 0.5 $cm^2$ squares. Control pellets were made by adding 5 μg of methylalcohol, a solvent for DHA and EPA, to each square and allowing it to dry.

Measured amounts of test substances DHA and EPA (DHA: 1.5; 5; 10; 30; 50; 75; 100; 300; 500; and 750 μg; EPA: 1.5; 10; 30; 50; 75; 100; 150; 300; 500; 700 μg) were added to each square in a 0.05% $CH_3OH$ solution. These were allowed to dry.

The pellets were then used in CAM assays following Auerbach, et al., Developmental Biology 41: 391-4 (1974). Four day old fertilized chicken eggs were cracked into plastic Petri dishes. The Peri dishes containing embryo were then incubated in 37° C. humidity incubator for another five days. On day nine of the incubation the pellets bearing either the test substance or control were applied to the CAM. The eggs were examined 48 and 72 hours after application of the pellets. The CAMs were then scored as positive ("+") or negative ("−") using the criteria based upon the published work of Folkman et al., Int. Rev. Exp. Path., 16: 207 (1976). A positive response is the production of "spoke-wheel" pattern around the pellet (see FIGS. 2 and 4). All assays were performed in multiple runs, and tests were performed, when possible, using material (DHA and EPA) from different suppliers.

The results are presented in Tables 1 and 2, as follows:

TABLE 1

| | CAM Assay with Docosahexaenoic acid (DHA) | | | | | |
|---|---|---|---|---|---|---|
| | Supplier: Sigma | | Supplier: Calbiochem | | Pooled Results | |
| μg/pel | score pos/total | % pos. | score pos/total | % pos. | score pos/total | % pos |
| 750 | 10/10 | 100 | — | — | 10/10 | 100 |
| 500 | 23/23 | 100 | — | — | 23/23 | 100 |
| 300 | 16/17 | 94.1 | — | — | 16/17 | 94.1 |
| 100 | 9/12 | 75.0 | 12/13 | 92.3 | 21/25 | 84 |
| 75 | 18/40 | 45.0 | 18/18 | 100 | 36/58 | 62 |
| 50 | 10/49 | 20.4 | 10/13 | 76.9 | 20/62 | 32.25 |
| 30 | 2/8 | 25 | 5/16 | 31.25 | 7/24 | 29.1 |
| 10 | 0/13 | 0 | 3/13 | 23.1 | 3/26 | 11.5 |
| 5 | 0/13 | 0 | 2/8 | 25 | 2/21 | 9.5 |
| 1.5 | 0/16 | 0 | 0/16 | 0 | 0/32 | 0 |

TABLE 2

| | CAM Assay with Eicosapentaenoic (EPA) | | | | | |
|---|---|---|---|---|---|---|
| | Supplier: Sigma | | Supplier: Calbiochem. | | Pooled Results | |
| μg/pel | score pos/total | % pos. | score pos/total | % pos. | score pos/total | % pos. |
| 700 | 12/12 | 100.0 | — | — | 12/12 | 100 |
| 500 | 9/9 | 100.0 | — | — | 9/9 | 100 |
| 300 | 11/11 | 100.0 | — | — | 11/11 | 100 |
| 150 | 8/8 | 100.0 | — | — | 8/8 | 100 |
| 100 | 11/12 | 91.7 | 13/14 | 93.0 | 23/26 | 92.3 |
| 75 | — | — | 6/6 | 100.0 | 6/6 | 100 |
| 50 | — | — | 9/12 | 75.0 | 9/12 | 75 |
| 30 | 7/11 | 63.6 | 7/14 | 50.0 | 14/25 | 56 |
| 10 | 0/11 | 0.0 | 2/20 | 10.0 | 2/31 | 6.45 |
| 1.5 | 1/9 | 11.1 | 0/10 | 0.0 | 1/19 | 5.26 |

Figure 2:
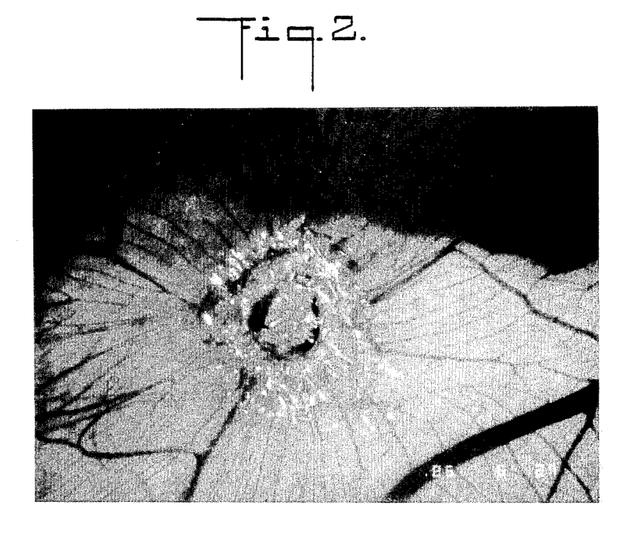
FIG. 2 depicts a chicken chorio-allantoic membrane responding to administration of DHA.
Figure 3:
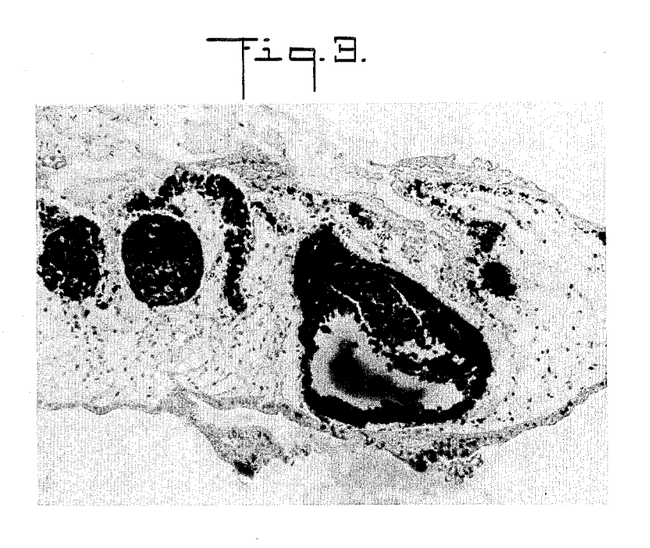
FIG. 3 shows histological sectioning of a chorio-allantoic membrane after application of DHA.

The results of these assays can be seen pictorially and graphically in FIGS. 2–5 and 8–11. In FIG. 2, one sees a low power view of a CAM assay using 300 μg of DHA in a pellet. Attention is drawn to the radial orientation of blood vessels toward the application site, and the large vessel loops pointing toward the pellet. In FIG. 3, a histological section of a CAM assay using the 300 μg sample of DHA 48 hours after application is shown. One sees thickening of the membrane, together with prominence and congestion of blood vessels, together with strong edema and mild proliferation of exoderm and endoderm. There are no signs of infiltration of inflammatory cells.

Figure 4:
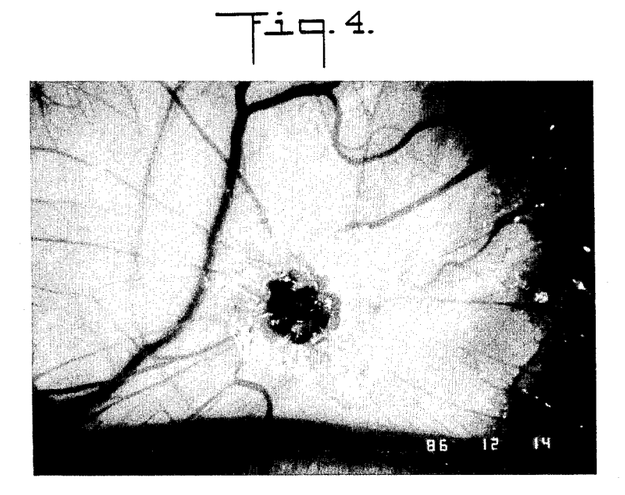
FIG. 4 shows a chicken chorio-allantoic membrane after administration of EPA.
Figure 5:
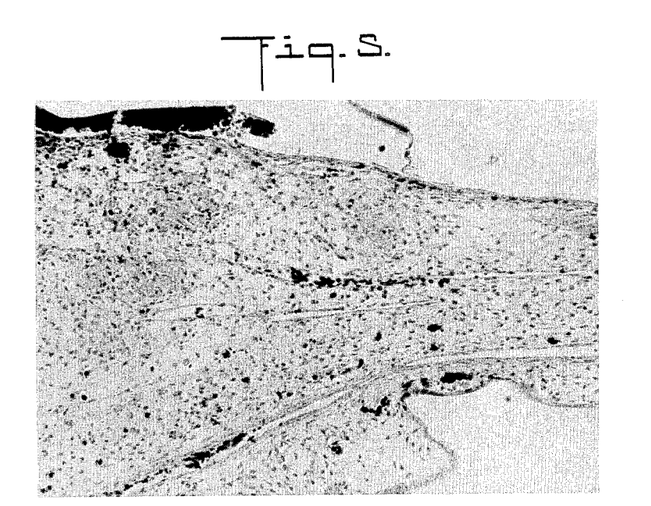
FIG. 5 shows histological sectioning of a chorio-allantoic membrane after application of EPA.

FIGS. 4 and 5 show the results obtained using 300 μg of EPA, 48 hours after application. As in FIG. 2, there is a radial or "spoke wheel" pattern of vessel distribution, together with bending of vascular loops toward the application site. This, of course, is a positive response. The histological sectioning shown in FIG. 4 shows membrane thickening, together with an increase in vessel number, and mild mesenchymal cell proliferation.

The graphs (FIGS. 8–11), merit some comment. The scatter plot for the CAM results for EPA from Sigma, and the plot for EPA from Sigma and Calbiochem (FIGS. 8 and 9), show sharp increases in CAM response, followed by plateauing at 75 μg/pellet, (Sigma), or 100 μg/pellet (combined). This is indicative of a dose related response. The same can be said for FIGS. 10 and 11, which parallel FIGS. 8 and 9 for DHA. The plateau, in both instances, is reached at about 100 μg/pellet.

EXAMPLE 2: Rabbit Cornea Assays

As stated supra, the rabbit cornea assays were performed following Alderman, et al., Biochemistry 24: 7866 (1986).

Subject rabbits were anesthetized via intramuscular injection of a solution of Ketamine/Rompun. Local anesthesia was applied in the form of intraconjunctival injection of 2% lidocoine hydrochloride.

Following anesthetization, a 3–4 mm slit was made at the apex of the cornea of each eye and a pocket extending to within 2 mm of the corneal limbus was produced using a apatula. In control animals, a blank methyl cellulose pellet was introduced into the corneal pocket, and the cornea was then extensively irrigated with normal saline solution. The experimental animals received DHA in the form of a methylcellulose pellet, prepared as in Example 1 supra. After surgery, 1% chloramphenicol ophthalmic ointment was applied to the eye, and the eye was then loosely taped shut to avoid drying and infection prior to the dissipation of the effect of the anesthesia.

Examination of the eyes took place 7 and 14 days afterward. The criterion was the presence of infiltrating vessels which extended toward the pellet implant. Signs of corneal inflammation were noted. A result was deemed positive if the above criterion was satisfied, and there was an absence of grossly visible signs of inflammation, such as cornea opacity.

Figure 6:
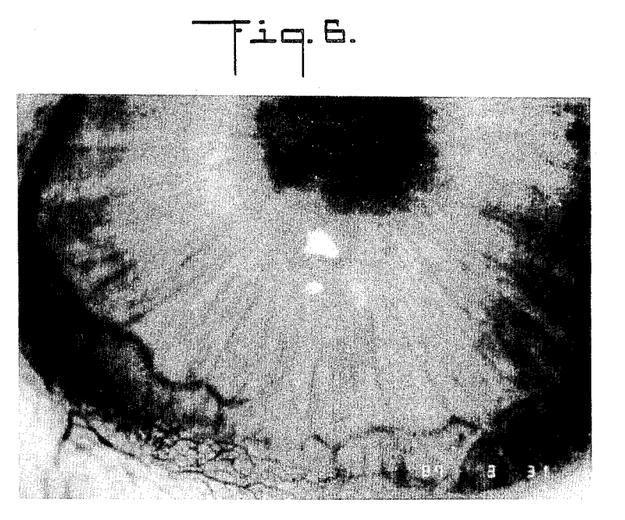
FIG. 6 shows the result of a control assay on rabbit cornea.
Figure 7:
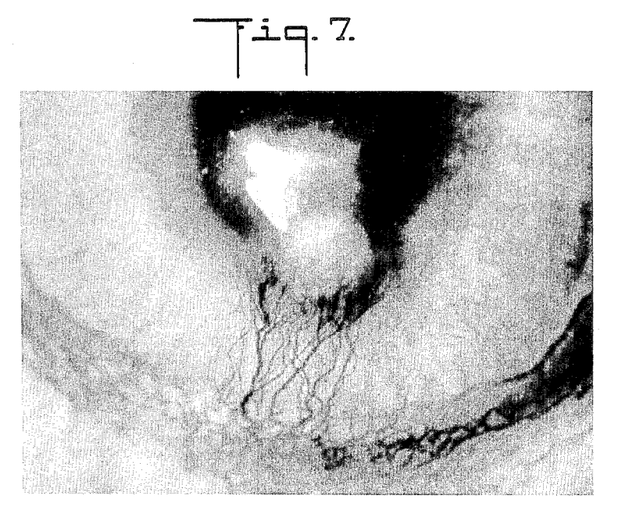
FIG. 7 shows angiogenesis in a rabbit cornea assay using DHA.
Figure 8:
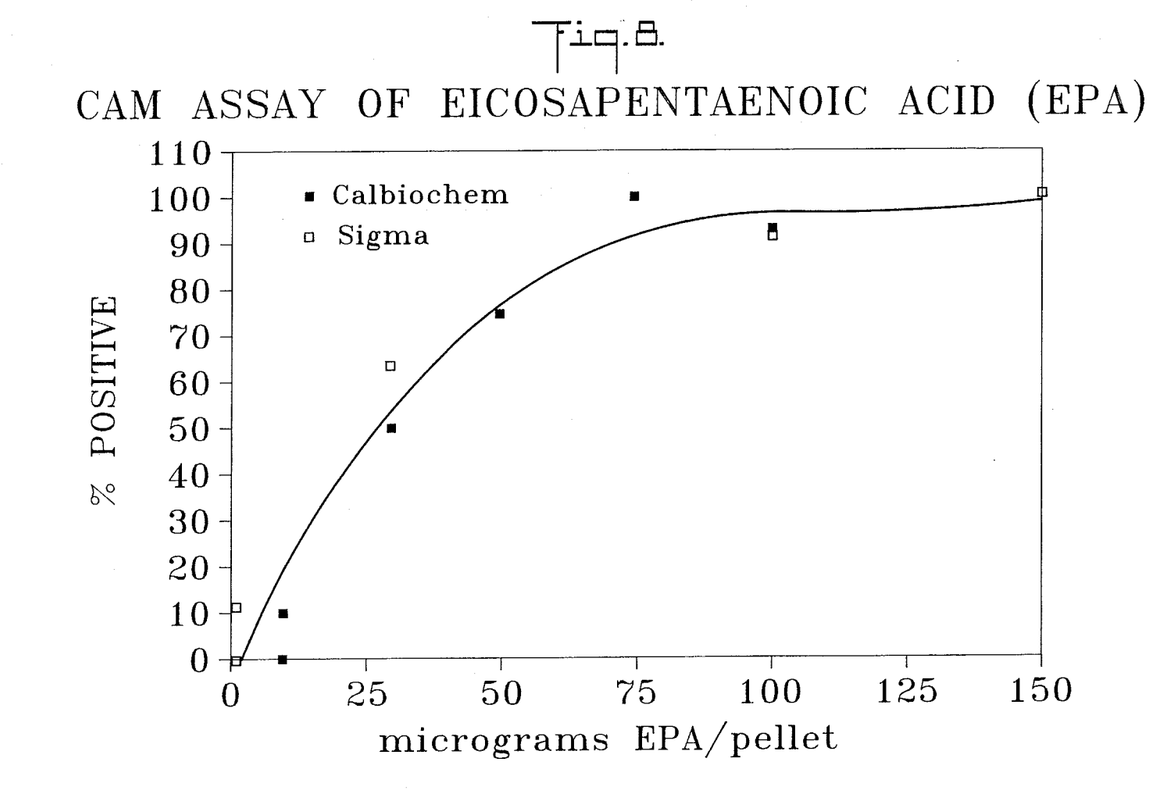
FIG. 8 is a scatter plot of chorio-allantoic membrane assays for EPA.
Figure 9:
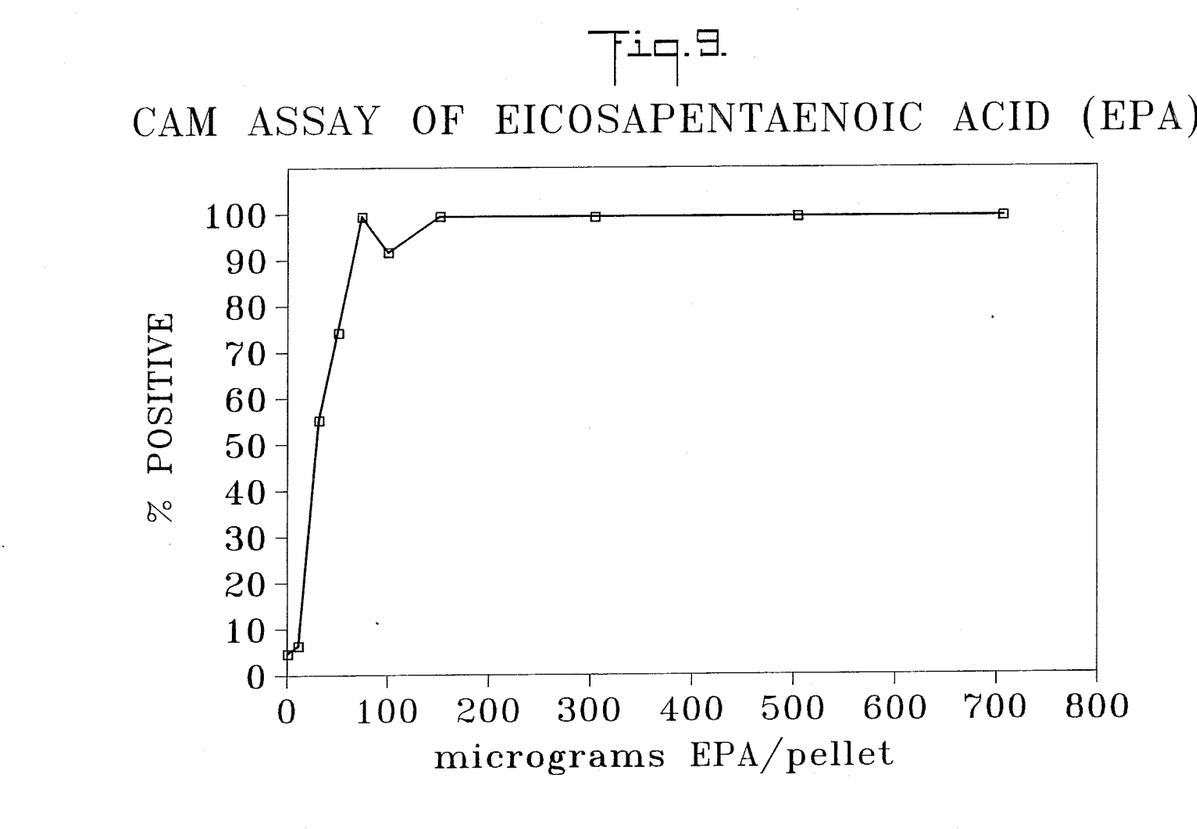
FIG. 9 shows a plot of chorio-allantoic membrane assay results for EPA.
Figure 10:
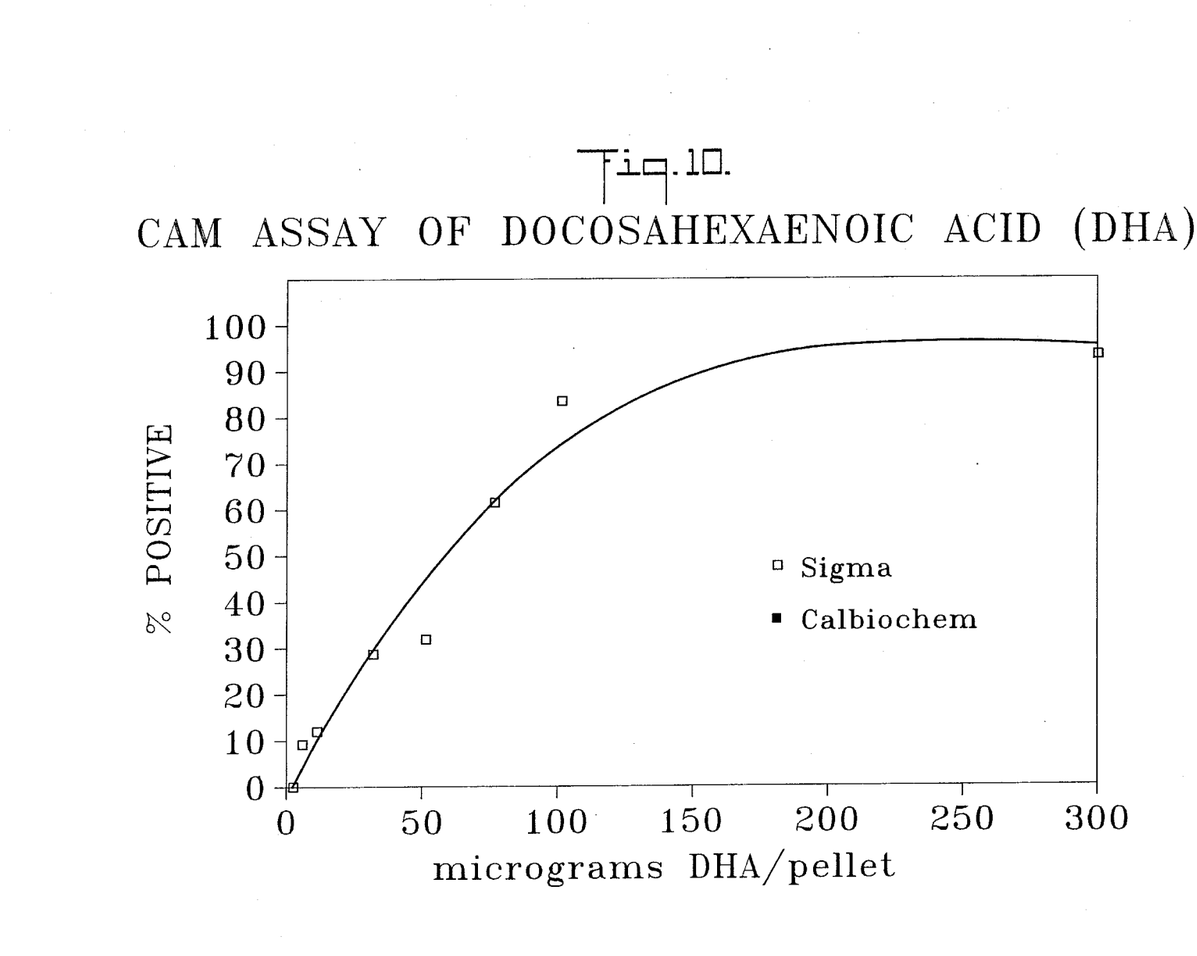
FIG. 10 shows a scatter plot for chorio-allantoic membrane assays for DHA.
Figure 11:
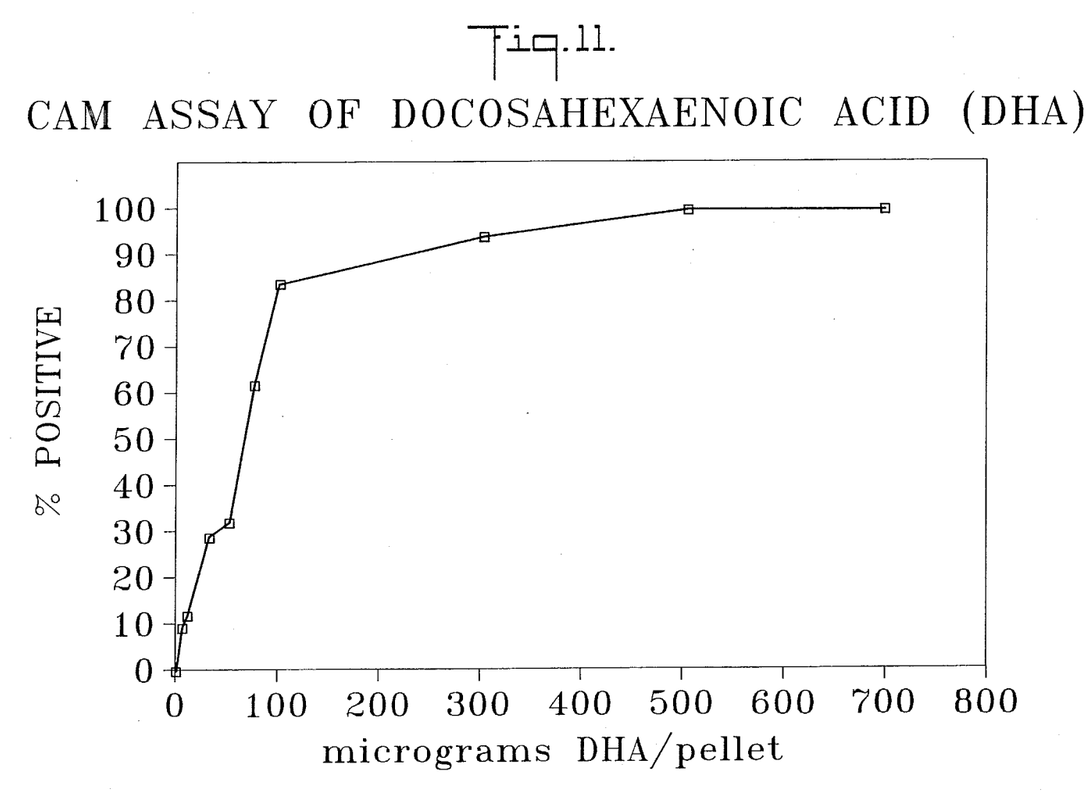
FIG. 11 shows a plot for chorio-allantoic membrane assays for DHA.

All six of the experimental rabbits (5.0 or 0.5 μg DHA), showed directional vascular growth from the limbus toward the pellet implantation site, without signs of inflammation. This can be seen, for example, in FIG. 6. After fourteen days, while the density of vascular growth varied from weak to strong, all experimental animals showed angiogenesis. In contrast, as seen in FIG. 5, none of the control animals showed any positive angiogenic effect.

The foregoing data stand as proof that omega-3 polyunsaturated fatty acids possess angiogenic activity, and can be used to provoke or to enhance angiogenesis in subjects. The CAM assay, as can be seen via reference to, e.g., U.S. Pat. No. 4,710,490 has been used to predict angiogenic effect in mammalian subjects. Such was also the case in the examples discussed supra.

Angiogenesis from the omega-3 PUFAs will be seen to occur when the angiogenic substance is administered to the subject in an angiogenically effective amount. This will vary, based upon the subject's age, size, general physical condition, etc., but in general the angiogenically effective amount will range from about 100 μg to about 20 mg per day. The mode of dosing and administering the angiogenic compound will vary, but it is preferred that the compound be administered directly to the site of required angiogenesis. This means that modes of administration such as injections, intramuscular and intradermal injection, and topical administration are preferred. Topical administration can take the form of e.g., administration in a lotion, an ointment, a creme, salve or unguent. Additionally, the angiogenically active compound may be impregnated in a dressing, such as a bandage, for controlled, continuous dosing to the subject.

While the ω-3 PUFAs are administrable in their pure form, it will easily be recognized to the skilled artisan that various adjuvants, carriers, diluents, and so forth may be used in combination with the ω-3 PUFAs in order to best effectuate their delivery. All such combinations and variations are encompassed by this invention.

The terms and expressions which have been employed are used as terms of description and not of limitation, and there is no intention in the use of such terms and expressions of excluding any equivalents of the features shown and described or portions thereof, it being recognized that various modifications are possible within the scope of the invention.

We claim:

1. Method for provoking or enhancing angiogenesis in a subject in need of enhanced angiogenic activity comprising locally administering to said subject an angiogenically active omega-3 polyunsaturated fatty acid in an angiogenically effective amount.

2. Method of claim 1, wherein said omega-3 polyunsaturated fatty acid is eicosapentaenoic acid.

3. Method of claim 1, wherein said omega-3 polyunsaturated fatty acid is docosahexaenoic acid.

4. Method of claim 1, comprising administering said omega-3 polyunsaturated fatty acid in the form of an ointment, lotion, salve or dressing.

5. Method of claim 1, wherein said omega-3 polyunsaturated fatty acid is administered in an amount ranging from about 100 μg to about 20 mg per day per subject.

6. Method for provoking or enhancing angiogenesis in a subject in need of enhanced agiogenic activity consisting of locally administering to said subject an angiogenically active omega-3 polyunsaturated fatty acid in an angiogenically effective amount.

7. Method of claim 6, wherein said omega-3 polyunsaturated fatty acid is eicosapentanoic.

8. Method of claim 6, wherein said omega-3 polyunsaturated fatty acid is docosahexaenoic acid.

* * * * *